United States Patent [19]
Modrovich et al.

[11] Patent Number: 5,910,422
[45] Date of Patent: *Jun. 8, 1999

[54] STABLE SINGLE LIQUID ALPHA-AMYLASE REAGENT

[75] Inventors: Ivan E. Modrovich; Shing S. Kwan, both of Camarillo; Leon C. Wortham, Canoga Park, all of Calif.

[73] Assignee: Medical Analysis Systems, Inc., Camarillo, Calif.

[ * ] Notice: This patent is subject to a terminal disclaimer.

[21] Appl. No.: 07/700,996

[22] Filed: May 10, 1991

Related U.S. Application Data

[63] Continuation of application No. 07/074,569, Jul. 17, 1987, abandoned.

[51] Int. Cl.⁶ ....................................... C12Q 1/40
[52] U.S. Cl. .............................. 435/22; 435/188; 435/269
[58] Field of Search .................................. 424/94.2, 94.3; 435/14, 18, 22, 188, 201, 269, 810; 436/8, 15, 18, 164, 811

[56] References Cited

U.S. PATENT DOCUMENTS

| | | |
|---|---|---|
| 4,086,139 | 4/1978 | Hoerle . |
| 4,102,747 | 7/1978 | Driscoll et al. . |
| 4,169,765 | 10/1979 | Keyes . |
| 4,172,765 | 10/1979 | Keyes . |
| 4,231,999 | 11/1980 | Carlson et al. . |
| 4,304,854 | 12/1981 | Nix et al. . |
| 4,310,625 | 1/1982 | Modrovich ................. 435/14 |
| 4,337,310 | 6/1982 | Batz et al. . |
| 4,427,771 | 1/1984 | Misaki et al. . |
| 4,473,645 | 9/1984 | Horwath . |
| 4,505,756 | 3/1985 | Nix et al. . |
| 4,536,477 | 8/1985 | Katkocin et al. . |
| 4,544,631 | 10/1985 | Rauscher et al. . |
| 4,550,077 | 10/1985 | Woodbridge et al. ..................... 435/14 |
| 4,613,570 | 9/1986 | Zeman . |
| 4,649,108 | 3/1987 | Blair ......................................... 435/22 |

FOREIGN PATENT DOCUMENTS 0085348  8/1983  European Pat. Off. .

OTHER PUBLICATIONS

Back et al, "Increased Thermal Stability of Proteins in the Presence of Sugars and Polyols" Biochemisty, V. 18(23) 5191–5196, 1979.

Maniatis et al; *Molecular Cloning, A Laboratory Manual*, pp. 443–454, 1982 Cold Spring Harbor Publications, Cold Spring, Harbor, New York.

*Primary Examiner*—Ralph Gitomer
*Attorney, Agent, or Firm*—Fish & Richardson P.C.

[57] ABSTRACT

A stable, single liquid alpha-amylase assay reagent comprises a polysaccharide or long chain oligosaccharide substrate for alpha-amylase having an optically detectable label bonded to the reducing end glucose, by a bond cleavable by alpha- or beta-glucosidase, and a blocking group bonded to the terminal end glucose. The reagent further comprises beta-amylase and either alpha- or beta-glucosidase. Sorbitol is provided in an amount of about 5% to retard degradation of the enzymes. Zwitterionic buffers are also provided to stabilize the enzymes. In preparing the reagent, the enzymes and substrate are filtered through a 0.2 micron or less filter to remove alpha-amylase producing organisms.

55 Claims, No Drawings

STABLE SINGLE LIQUID ALPHA-AMYLASE REAGENT

This application is a continuation of Ser. No. 07/074,569 filed on Jul. 17, 1987, now abandoned.

FIELD OF THE INVENTION

This invention relates generally to reagents for determining serum levels of alpha-amylase and, more particularly, to a stables single-liquid alpha-amylase assay reagent.

BACKGROUND OF THE INVENTION

Alpha-amylase is found primarily in the pancreas and salivary glands. When released in the digestive tract, the enzyme hydrolyses starch. Alpha-amylase determinations are useful in the diagnosis of diseases of the pancreas and parotids. Elevated serum levels are associated with acute pancreatitis and other pancreatic disorders, as well as mumps and bacterial parotitis. Decreased serum values may be found with liver diseases, such as hepatitis and obstructive jaundice, and liver tumors or abscesses.

Historically, methods for determining alpha-amylase in serum have included viscosimetric, turbidimetric, iodometric, and reductometric technology. With these methodologies, reaction times are long, endogenous glucose tends to interfere, reaction colors are unstable, and reproducibility is poor. Recently, assay systems for the determination of alpha-amylase have been developed.

Such assay systems for alpha-amylase typically include a reagent comprising a polysaccharide or oligosaccharide substrate with a label, e.g., a chromogen unit, attached. The substrate is hydrolyzed by alpha-amylase to form one or two smaller oligosaccharides. The reagent further comprise one or more enzymes which further hydrolyze the smaller oligosaccharides to free the label unit which can then be detected spectrophotometrically.

Such assay reagents enable rapid and accurate determinations of alpha-amylase compared to historical methodologies. However, the stability of such reagents is poor. Consequently, assay reagents are generally stored in a lyophilized state and must be reconstituted prior to use. Once reconstituted, the shelf life is generally only one to fourteen days. Moreover, such reagents tend to give variable and often undesirably high background levels which adversely affect the consistency and accuracy of this system.

SUMMARY OF THE INVENTION

According to the present invention, there is provided a stable, single-liquid alpha-amylase assay reagent for the rapid determination of alpha-amylase in biological fluids The assay reagent comprises an aqueous solution substantially free of alpha-amylase and/or alpha-amylase activity containing at least one substrate which is cleavable directly or indirectly by alpha-amylase to produce a detectable change in the reaction mixture. The detectable change may be the production or elimination of a detectable component. Such components may be detected by any suitable means including optical, electrochemical and thermochemical means.

In a preferred embodiment of the invention, the reagent comprises a polysaccharide or long-chain oligosaccharide substrate having a label attached at the reducing end. The substrate is hydrolyzable by alpha-amylase to form short-chain oligosaccharides, at least one of which comprises the labels The reagent further comprises at least one exo-enzyme, and preferably a pair of exo-enzymes, preferably beta-amylase and alpha- or beta-glucosidase, which further hydrolyses the oligosaccharides to free the label which is then detectable spectrophotometrically. The rate at which the free label is formed provides a direct indication of the concentration of alpha-amylase in the biological fluid.

The alpha-amylase reagent is made substantially free of alpha-amylase by utilizing sterile water and purified reagents, and by passing the exo-enzymes and substrate, either individually or in combination, through a filter having a pore size of not more than about 0.2 micron to remove alpha-amylase-producing bacteria. Elimination of alpha-amylase from the reagent eliminates the consumption of the substrate during storage and hence stabilizes the reagent.

The alpha-amylase assay reagent is further stabilized by the inclusion of a diol or polyol which retards the degradation of the exo-enzymes.

DETAILED DESCRIPTION OF THE INVENTION

In accordance with the present invention, there is provided an assay reagent for determining the concentration of alpha-amylase in biological fluids or sera. The assay reagent is a single, aqueous solution that is stable for at least six months and preferably for at least one year at about 2 to about 8° C. As used herein, the term "stable" means that the reagent maintains at least 95% recovery. For example, if the reagent, when first mixed, provides an alpha-amylase analysis of 100 units for a particular sample, the reagent is considered "stable" if, after a select period of time, e.g. six months, the reagent provides an analysis on the same sample of at least 95 units, i.e., 95% of the original analysis.

The addition of a biological fluid containing alpha-amylase to the reagent initiates a series of reactions resulting in the production of a detectable product, the rate of production of the detectible product being directly proportional to the concentration of alpha-amylase in the biological fluid.

The assay reagent comprises a substrate which is hydrolyzable by alpha-amylase, and, at least one and preferably a pair, of exo-enzymes. Preferred substrates and exo-enzymes are described in U.S. Pat. No. 4,649,108, assigned Genzyme Corporation incorporated herein by reference.

The substrate is preferably a polysaccharide or, more preferably an oligosaccharide that is hydrolyzable by alpha-amylase. The substrate preferably contains at preferably an oligosaccharide that is hydrolyzable by least three glucose units. The reducing end glucose unit of the substrate is bonded, by a bond which can be cleaved by alpha- or beta-glucosidase, to a label which exhibits an optically measurable change upon cleavage of the bond. The terminal glucose unit of the substrate is bonded to a blocking group which inhibits cleavage by exo-enzymes of the bond between the terminal glucose unit and the adjacent glucose unit.

The label is preferably a chromophores a fluorophore, a chemiluminescent substituent, or a bioluminescent substituent. Preferred labels include pnitrophenol, o-nitrophenol, coumarin derivatives such as 4-methylumbel-liferone and luciferin. Preferably, the substrate has eight or fewer glucose units and most preferably has six or seven. Preferred blocking substituents are acetals or ketals, e.g., benzylidene.

The presently preferred substrate is p-nitrophenyl-maltoheptaoside in which the terminal glucose group is blocked to prevent spontaneous hydrolysis and reactions with the exo-enzymes. This substrate is hydrolyzed by alpha-amylaseto formp-nitrophenylmaltotrioside, p-nitrophenylmaltotetraoside, and the blocked oligosaccharides maltotriose and maltotetraose. The substrate is preferably present in the reagent in a quantity that is sufficient so that the concentration of substrate is not rate-limiting. A concentration of about 2 mg/ml is presently preferred.

Preferably, the assay reagent comprises a pair of exo-enzymes that cooperates to free the label. Preferred exo-enzymes include beta-amylase, i.e., glucoamylase, and either alpha- or beta-glucosidase (depending on the nature of the bond between the label and the reducing end glucose) Once a substrate has undergone cleavage by alpha-amylase, beta-amylase acts to break the smaller oligosaccharides into single glucose units. Alpha- or beta-glucosidase then acts to free the label from the remaining glucose unit.

Because of the blocking group bonded to the terminal glucose unit of the substrate, neither exo-enzyme can act until alpha-amylase has acted. Accordingly, the exo-enzymes are not rate-limiting as long as they are present in quantities sufficient to fully and rapidly react with the products of the alpha-amylase cleavage. A concentration of beta-amylase of about 5 KIU/L and of alpha- or beta-glucosidase of about 12.5 KIU/L is presently preferred.

In addition to the substrate and the exo-enzymes, the assay reagent comprises a source of calcium, e.g., calcium chloride, and an additional source of chloride, e.g., sodium chloride. Calcium and chloride ions are required to activate the enzyme alpha-amylase. The calcium chloride and sodium chloride are present in sufficient amounts that neither the concentration of calcium nor chloride ions is rate-controlling. A calcium chloride concentration of about 5 mM and a sodium chloride concentration of about 50 mM are presently preferred.

In the practice of the invention, the assay reagent is stabilized by a combination of techniques. First, a water soluble diol or polyol is added to the reagent. Alpha- and beta-glucosidase have high rates of degradation Dihydric and polyhydric alcohols ("diols" and "polyols"). Polyols tend to retarded this process. Beta-amylase, while not as unstable as alpha- or beta-glucosidase, also undergoes degradation over time. This process is also retarded by diols or polyols. Preferred diols or polyols are selected from the group consisting of ethylene glycol, polyethylene glycol, glycerol, sorbitol, substituted glycols and mixtures .thereof. The presently preferred diol or polyol is sorbitol.

Accordingly, a dihydric or polyhydric alcohol, preferably sorbitol, is maintained in the reagent in a concentration sufficient to retard the degradation of the exo-enzymes without interfering adversely with reagent utility. While any presence of diol or polyol tends to retard degradation of the enzymes, it is preferred that the concentration of diol or polyol be maintained in the range of about 10 to about 300 grams per liter, preferably about 30 to about 70 grams per liter, and more preferably about 50 grams per liter. Below about 10 grams per liter, the reagent still exhibits poor stability. Above about 300 grams per liter, the reagent exhibits no further increase in stability, and the viscosity of the reagent tends to become undesirably high.

The enzymes and substrates are presently further stabilized by the addition of a buffer capable of maintaining the reagent at a pH of from about 4 to about 10 and preferably at a pH of from about 6.5 to about 7.5. Preferred buffers are zwitterionic buffers such as 3-N-morpholine propane sulfonic acid (MOPS), N-2-hydroxyethyl-piperazine-N'-2-ethane sulfonic acid (HEPES), tris (hydroxymethyl) methylaminopropane sulfonic acid (TAPS), or 3(N-tris (hydroxymethyl)methylamino)-2-hydroxy propane sulfonic acid (TAPSO). MOPS is presently preferred.

The zwitterionic buffer is preferably present in the range of from about 0.01 to about 1.0 moles per liter, and preferably 0.05 to about 0.1 moles per liter. Concentrations of zwitterionic buffers above about 0.1 molar are not preferred as such concentrations tend to create an high ionic strength in the reagent which tends to destabilize the enzymes. Concentrations below about 0.05 molar are not preferred because the beneficial effect of the zwitterionic buffer is diminished.

It is believed that the diol or polyol and the zwitterionic buffers retard degradation by associating with the enzymes, thereby preventing the association of other components which act on the enzymes detrimentally. It is also believed that the diol or polyol and/or zwitterionic buffers also prevent deactivation of the enzymes by maintaining the effective 3-dimensional configuration of the enzyme.

Beta-amylase and alpha- or beta-glucosidase are typically contaminated by microorganisms, such as diptheroides and pseudomonus maltophilia, which produce alpha-amylase. Accordingly, in the practice of the invention, the enzymes beta-amylase and alpha- or beta-glucosidase, and preferably the substrate are all filtered through a filter sufficiently small to remove the alpha-amylase-producing microorganisms Each enzyme may be filtered separately, or the enzymes and substrates may be combined before filtration. It has been found that a filter having a pore size no greater than about 0.2 microns is sufficient to remove alpha-amylase-producing bacteria.

It is understood that in addition to filtering the enzymes and substrate, it is important that there be no contamination of alpha-amylase-producing bacteria from other sources, such as the water or equipment used in preparing the reagent Hence, the equipment used must be sterile, e.g., autoclaved, and the water used in the reagent is distilled water or water which has been boiled.

While filtering of the enzymes removes substantially all of the alpha-amylase producing bacteria, it is still preferred to incorporate into the reagent one or more antimicrobial agents, i.e. agents toxic to microbial contaminants or at least capable of inhibiting or retarding microbial growths Such agents include cetyltrimethylammonium (CTMA) bromide, cobalt complexes such as $[C_o(NH_3)_4(H_2O)Cl]$ $SO_4$ and $[C_o((OH)$ $C_o(NH_3)_4)_3]$ $(SO_4)_3$ $4H_2O$, oyster glycogen, macrodextrin, bactrim, sodium azide, thimerosal, and sodium dodecyl sulfate. The presently preferred antibiotic agents include cetyltrimethylammonium (CTMA) bromide in a concentration of about 0.001%, bactrim in an amount of about 0.075 mg/ml, and sodium azide in an amount of about one gram per liter.

In preparing the reagent, all of the components can be mixed together in a batch mixing process. However, because of the high expense of the enzymes and substrate, it is preferred to initially prepare stock solutions of the buffer, an enzyme concentrate and a substrate.

For large-scale production, preparation of separate stock buffer solution, enzyme concentration, and substrate concentrate enables mixing of small quantities of the component solutions and testing for contamination before mixing the entire stock of enzyme and substrate concentrates with the buffer solution.

EXAMPLE

A stable, single-liquid alpha-amylase reagent was prepared by first preparing a buffer solution, an enzyme concentrate, and a substrate concentrate.

The buffer solution was prepared by adding 1.0 liter of sterile, e.g., distilled, water to a sterile, e.g., autoclaved, stainless steel compounding container. 10.460 grams MOPS was then added to the water. The pH was measured and, if needed, was adjusted to 7.0±0.03 with 4.0 M sodium hydroxide While mixing, the following components were added: 0.740 grams of the disodium salt of EDTA; 1.030 grams calcium chloride; 2.920 grams sodium chloride; 50.0 grams sorbitol (purified); 1.0 grams sodium azide; 2.50 ml Bactrim solution (in DMSO); and 1.0 ml 1% CTMA bromide. The mixture was stirred for ten minutes, and then the pH was measured. If needed, the pH is adjusted to 7.0+/±0.03 with 4 M sodium hydroxide or 6 M hydrochloric acid. The buffer solution is then filtered through an autoclaved 0.2 micron filter into 100 ml reagent bottles which were sterilized with ethylene oxide.

The enzyme concentrate was prepared by introducing 0.9660 liter of sterile water into a sterile stainless steel container. 10.460 grams MOPS was then added to the water. The pH was measured and adjusted to 7.0±±±0.03 with 4 M sodium hydroxide. While mixing, the following components were added: 0.742 disodium EDTA; 1.030 grams calcium chloride; 2.920 grams sodium chloride; 50.0 grams sorbitol (purified); 1.0 gram sodium azide; 2.50 ml bactrim solution (in DMSO); and 1.0 ml 1% CTMA bromide. To this solution was added, without mixing, 2500.0 KIU maltase (alpha-glucosidase) and 1000.0 KIU glucoamylase (beta-amylase) Once the enzymes were dissolved, the mixture was stirred gently for 10 minutes and then filtered through an autoclaved 0.2 micron filter into an autoclaved pipettor. The filtered solution was stored at 2–8° C. for 24 hours before using.

The substrate concentrate was prepared in the same manner as the enzyme concentrate except that, instead of the enzymes, 200.0 grams p-nitrophenylmaltoheptaoside was added and mixed slowly to dissolve and then stirred for 15 minutes The substrate concentrate was then filtered through an autoclaved 0.2 micron filter into an autoclaved pipettor.

The alpha-amylase reagent was then prepared by dispensing, under aseptic conditions, 1.0 ml of the enzyme concentrate and 1.0 ml of the substrate concentrate into the 100 ml reagent bottles containing buffer solution.

The preceding description has been presented with reference to present preferred embodiments of the invention. Workers skilled in the art and technology to which this invention pertains will appreciate that alterations and changes in the described composition and procedures can be practiced without meaningfully departing from the principle spirit and scope of the invention.

Accordingly, the foregoing description should not be read as pertaining only to the precise compositions and procedures described, but rather should be read consistent with and as support for the following claims which are to have their fullest fair scope.

What is claimed is:

1. A single liquid alpha-amylase reagent composition comprising an aqueous solution which is substantially free of alpha-amylase producing microorganisms which comprises:

at least one substrate which is hydrolyzed when mixed with a sample of body fluid containing alpha-amylase to yield directly or indirectly by a reaction involving alpha-amylase to form a detectable label released to the reaction mixture, the rate of formation of said detectable label to the reaction mixture being proportional to the amount of alpha-amylase present in the sample and at least one exo-enzyme to cooperate with the alpha-amylase in the formation of the detectable label; and a compound selected from the group consisting of diols and polyols present in an amount sufficient to stabilize the exo-enzymes, said substrate being present in a concentration sufficient to prevent the substrate from limiting the rate of hydrolysis thereof , said reagent composition being stable against substrate and enzyme degradation for at least 6 months at 2 to 8° C.

2. An alpha-amylase assay reagent according to claim 1 wherein the substrate comprises an optically detectable label cleavable directly or indirectly by alpha-amylase.

3. An alpha-amylase assay reagent according to claim 1 further comprising at least one enzyme and wherein the substrate reacts with alpha-amylase to produce a product which then reacts with the, enzyme to produce a detectable change in the reaction mixture.

4. A single liquid alpha-amylase reagent according to claim 1, wherein the compound is selected from the group consisting of diol and polyol is selected from the group consisting of ethylene glycol, polyethylene glycol, sorbitol, substituted glycols and mixtures thereof.

5. A single liquid alpha-amylase reagent comprising an aqueous solution substantially free of alpha-amylase which comprises:

a substrate selected from the group consisting of polysaccharides and oligosaccharides, which substrate is hydrolyzable by alpha-amylase and having an optically detectable label, bonded to the substrate which is cleavable by alpha-glucosidase or beta-glucosidase, to the reducing end glucose of the substrate and a blocking group bonded to the terminable end glucose of the substrate, said alpha-amylase releasing the group from substrate label at a rate proportional to alpha-amylase concentration in a sample to enable formation of the label, said substrate present in a quantity sufficient not to limit the rate of hydrolysis;

an exo-enzyme capable of cleaving the bond between the label and the reducing end glucose of the substrate selected from the group consisting of alpha-glucosidase and beta-glucosidase; and a compound selected from the group consisting of diols and polyols present in an amount sufficient to retard the degradation of the enzymes in the reagent said alpha-amylase reagent being stable for at least six months at 2 to 8° C.

6. An alpha-amylase reagent according to claim 5 wherein the diol or polyol is selected from the group consisting of ethylene glycol, polyethylene glycol, sorbitol, and mixtures thereof.

7. An alpha-amylase assay reagent according to claim 5 wherein the diol or polyol is present in an amount of from about 10 to about 300 grams per liter of the reagent.

8. An alpha-amylase assay reagent according to claim 7 wherein the diol or polyol is present in an amount of about 30 to about 70 grams per liter of the reagent.

9. An alpha-amylase assay reagent according to claim 5 further comprising at least one buffer capable of maintaining the reagent at a pH of from about 4 to about 10.

10. An alpha-amylase assay reagent according to claim 9 wherein the buffer maintains the reagent at a pH of from about 6.5 to about 7.5.

11. An alpha-amylase assay reagent according to claim 9 wherein the buffer is a zwitterionic buffer capable of stablizing at least one of the enzymes of the reagent.

12. An alpha-amylase assay reagent according to claim 11 wherein the zwitterionic buffer is present in an concentration of from about 0.01 to about 1.0 moles per liter.

13. An alpha-amylase assay reagent according to claim 11 wherein the zwitterionic buffer is selected from the group consisting of MOPS, HEPES, TAPS, TAPSO and mixtures thereof.

14. An alpha-amylase assay reagent according to claim 13 wherein the zwitterionic buffer is MOPS.

15. An alpha-amylase assay reagent according to claim 5 wherein at least the enzymes have been passed through a filter having a pore size sufficiently small to retain substantially all alpha-amylase producing microorganisms.

16. An alpha-amylase assay reagent according to claim 15 wherein the filter has a pore size of no more than about 0.2 micron.

17. An alpha-amylase assay reagent according to claim 5 wherein the enzymes and the substrate have been passed through a filter having a pore size sufficiently small to retain substantially all alpha-amylase producing microorganisms.

18. An alpha-amylase assay reagent according to claim 17 wherein the filter has a pore size of no more than about 0.2 microns.

19. An alpha-amylase assay reagent according to claim 5 further comprising at least one antimicrobial agent.

20. An alpha-amylase assay reagent according to claim 19 wherein the antimicrobial agent is selected from the group consisting of CTMA bromide, bactrim, sodium azide, and mixtures thereof.

21. A method for preparing a stable, single liquid alpha-amylase assay reagent comprising:
   introducing at least one buffer into sterile water to provide a buffer solution having a pH of about 6.5 to about 7.5;
   introducing into the buffer solution a polysaccharide or oligosaccharide substrate for alpha-amylase having an optically detectable label bonded, by a bond cleavable by alpha-glucosidase or beta-glucosidase, and a blocking group bonded to each terminal end glucose of the substrate;
   beta-amylase;
   an exo-enzyme capable of cleaving the bond between the label and the substrate selected from the group consisting of alpha-glucosidase and beta-glucosidase; and
   at least one diol or polyol present in an amount sufficient to retard the degradation of the enzymes in the reagent; and
   passing the substrate and enzyme containing solution through a filter having a pore size sufficiently small to remove substantially all alpha-amylase producing microorganisms.

22. A method according to claim 21 wherein the diol or polyol is introduced in an amount of from about 10 to about 300 grams per liter of the buffer solution.

23. A method according to claim 22 wherein the diol or polyol is introduced in an amount of about 30 to about 70 grams per liter of the buffer solution.

24. A method according to claim 21 wherein the buffer is zwitterionic buffer capable of stabilizing at least one of the enzymes of the reagent.

25. A method according to claim 24 wherein the zwitterionic buffer is introduced in a concentration of from about 0.01 to about 1.0 moles per liter.

26. A method according to claim 24 wherein the zwitterionic buffer is selected from the group consisting of MOPS, HEPES, TAPS, TAPSO and mixtures thereof.

27. A method according to claim 25 wherein the zwitterionic buffer is MOPS.

28. A method according to claim 21 further comprising introducing into the buffer solution at least one antimicrobial agent.

29. A method according to claim 28 wherein the antimicrobial agent is selected from the group consisting of CTMA bromide, bactrim, sodium azide, and mixtures thereof.

30. A method for preparing a stable, single liquid alpha-amylase assay reagent comprising:
   preparing a buffer solution having a pH of from about 6.5 to about 7.5 comprising at least one buffering agent and sorbitol;
   introducing into a first portion of the buffer solution polysaccharide or oligosaccharide substrate for alpha-amylase having an optically detectable label bonded, by a bond cleavable by alpha-glucosidase or beta-glucosidase, to the reducing end glucose of the substrate and a blocking group bonded to the terminal end glucose of the substrate;
   introducing into a second portion of the buffer solution beta-amylase and an exo-enzyme capable of cleaving the bond between the label and the reducing and glucose of the substrate selected from the group consisting of alpha-glucosidase and beta-glucosidase; and
   filtering each of the first and second portions of the buffer solution through a filter having a pore size of no greater than about 0.2 microns; and
   mixing the first and second portions of the buffer solution.

31. A method according to claim 30 wherein sorbitol is present in an amount of from about 10 to about 300 grams per liter of the buffer solution.

32. A method according to claim 30 wherein sorbitol is present in an amount of from about 30 to about 70 grams per liter of the reagent.

33. A method according to claim 30 wherein the buffer is a zwitterionic buffering agent capable of stabilizing at least one of the enzymes of the reagent.

34. A method according to claim 33 wherein the zwitterionic buffering agent is present in a concentration of from about 0.01 to about 1.0 moles per liter.

35. A method according to claim 33 wherein the zwitterionic buffer is selected from the group consisting of MOPS, HEPES, TAPS, TAPSO and mixtures thereof.

36. A method according to claim 35 wherein the zwitterionic buffering agent is MOPS.

37. A method according to claim 36 wherein the antimicrobial agent is selected from the group consisting of CTMA bromide, bactrim, sodium azide, and mixtures thereof.

38. A method according to claim 30 wherein the buffer solution further comprises at least one antimicrobial agent.

39. A stable, single liquid alpha-amylase reagent comprising an aqueous solution substantially free of alpha-amylase producing microorganisms which comprises:
   a polysaccharide or oligosaccharide substrate hydrolyzable by alpha-amylase and having an optically detectable label bonded, by a bond cleavable by alpha-glucosidase or beta-glucosidase, to the reducing end glucose of the substrate and a blocking group bonded to the terminal end glucose of the substrate, said substrate being present in a concentration of at least 2 mg/ml of reagent and hydrolyzed in the presence of alpha-amylase to yield the label at a rate proportional to the concentration of alpha-amylase in a biological fluid;
   beta-amylase in a concentration of about 5 KIU/L;
   an exo-enzyme capable of cleaving the bond between the label and the reducing end glucose of the substrate selected from the group consisting of alpha-glucosidase and beta-glusidase, said exo-enzymes being present in a concentration of about 12.5 KIU/L;
   a polyol present in an amount of from about 10 to 300 grams per liter and sufficient calcium chloride in a concentration of about 5 mM and to retard said reagent buffered by a zwitterionic buffer to a pH of from about 4 to about 10 and being stable for at least 6 months at 2 to 8° C.

40. An alpha-amylase assay reagent according to claim 39 wherein the polyol is sorbitol.

41. An alpha-amylase assay reagent according to claim 40 wherein the sorbitol is present in an amount of about 30 to 70 grams per liter of the reagent.

42. An alpha-amylase assay reagent according to claim 41 in which the buffer maintains the reagent at a pH of from about 6.5 to about 7.5.

43. An alpha-amylase assay reagent according to claim 42 the substrate is p-nitrophenylmaltoheptaoside.

44. An alpha-amylase assay reagent according to claim 42 wherein the enzymes and the substrate have been passed through a filter having a pore size no more than about 0.2 micron and sufficiently small to retain substantially all alpha-amylase producing microorganisms.

45. An alpha-amylase assay reagent according to claim 44 further comprising at least one antimicrobial agent.

46. An alpha-amylase assay reagent according to claim 45 wherein the antimicrobial agent is selected from the group consisting of CTMA bromide, bactrim, sodium azide, and mixtures thereof.

47. An alpha-amylase assay reagent according to claim 39 wherein the polyol is present in an amount of about 30 to about 70 grams per liter of the reagent.

48. An alpha-amylase assay reagent according to claim 39 wherein the zwitterionic buffer is present in an concentration of from about 0.01 to about 1.0 moles per liter.

49. An alpha-amylase assay reagent according to claim 45 wherein the zwitterionic buffer is selected from the group consisting of MOPS, HEPES, TAPS, TAPSO and mixtures thereof.

50. An alpha-amylase assay report reagent according to claim 39 wherein the zwitterionic buffer is selected from the group consisting of MOPS, HEPES, TAPS, TAPSO and mixtures thereof.

51. An alpha-amylase assay reagent according to claim 39 wherein the substrate is p-nitrophenylmaltoheptaoside.

52. An alpha-amylase assay reagent according to claim 39 wherein at least the enzymes have been passed through a filter having a pore size sufficiently small to retain substantially all alpha-amylase producing microorganisms.

53. An alpha-amylase assay reagent according to claim 52 wherein the filter has a pore size of no more than about 0.2 micron.

54. An alpha-amylase assay reagent according to claim 39 further comprising at least one antimicrobial agent.

55. An alpha-amylase assay reagent according to claim 54 wherein the antimicrobial agent is selected from the group consisting of CTMA bromide, bactrium, sodium azide, and mixtures thereof.

* * * * *